United States Patent
Stolin et al.

(10) Patent No.: US 8,335,363 B2
(45) Date of Patent: Dec. 18, 2012

(54) METHOD FOR IMAGE RECONSTRUCTION OF MOVING RADIONUCLIDE SOURCE DISTRIBUTION

(75) Inventors: Alexander V. Stolin, Newport News, VA (US); John E. McKisson, Hampton, VA (US); Seung Joon Lee, Knoxville, TN (US); Mark Frederick Smith, Catonsville, MD (US)

(73) Assignee: Jefferson Science Associates, LLC, Newport News, VA (US)

( * ) Notice: Subject to any disclaimer, the term of this patent is extended or adjusted under 35 U.S.C. 154(b) by 788 days.

(21) Appl. No.: 12/456,372

(22) Filed: Jun. 16, 2009

(65) Prior Publication Data

US 2010/0316275 A1   Dec. 16, 2010

(51) Int. Cl.
    *G06K 9/00* (2006.01)
(52) U.S. Cl. ........................................ 382/128
(58) Field of Classification Search ........... 382/128–134
    See application file for complete search history.

(56) References Cited

U.S. PATENT DOCUMENTS

| | | | |
|---|---|---|---|
| 7,209,579 B1 * | 4/2007 | Weisenberger et al. | 382/128 |
| 2007/0040122 A1 * | 2/2007 | Manjeshwar et al. | 250/363.03 |

OTHER PUBLICATIONS

Sang-Keun Woo, Hiroshi Watabe, Yong Choi, Kyeong Min Kim, Chang Choon Park, Peter M. Bloomfield, and Hidehiro Iida, Membet "Sinogram-Based Motion Correction of PET Images Using Optical Motion Tracking System and List-Mode Data Acquisition" (IEEE Transactions on Nuclear Science, vol. 51, No. 3, Jun. 2004).*
L Livieratos, L Stegger, P M Bloomfield, K Schafers, D L Bailey and P G Camici "Rigid-body transformation of list-mode projection data for respiratory motion correction in cardiac PET" (Phys. Med. Biol. 50 (2005) 3313-3322).*

* cited by examiner

*Primary Examiner* — Bernard Krasnic
*Assistant Examiner* — Weiwen Yang

(57) ABSTRACT

A method for image reconstruction of moving radionuclide distributions. Its particular embodiment is for single photon emission computed tomography (SPECT) imaging of awake animals, though its techniques are general enough to be applied to other moving radionuclide distributions as well. The invention eliminates motion and blurring artifacts for image reconstructions of moving source distributions. This opens new avenues in the area of small animal brain imaging with radiotracers, which can now be performed without the perturbing influences of anesthesia or physical restraint on the biological system.

2 Claims, 4 Drawing Sheets

METHOD FOR IMAGE RECONSTRUCTION OF MOVING RADIONUCLIDE SOURCE DISTRIBUTION

The United States of America may have certain rights to this invention under Management and Operating Contract DE-AC05-06OR23177 from the United States Department of Energy.

FIELD OF THE INVENTION

The present invention relates to radionuclide image reconstruction techniques and more particularly to such techniques that are useful in the imaging of moving radionuclide sources.

BACKGROUND OF THE INVENTION

For human and animal single photon emission computed tomography (SPECT) imaging, anesthesia and physical restraints may be used to reduce or eliminate motion, however these methods may directly influence the pharmacokinetics of the relevant biological system or cause stress that may indirectly affect radiotracer uptake and retention. These effects are pronounced in brain scanning. Imaging unanesthetized, unrestrained small animals can provide unique capabilities for biomedical research by eliminating the impact of anesthetic on the animal brain function and reducing the stress to the animal, thus opening new possibilities in the area of brain studies.

Conventional image reconstruction for emission computed tomography assumes that the source activity distribution and the human, animal or object being imaged are static. This assumption is not necessarily true for human imaging, where there may be some head or body motion, for imaging unanesthetized animals where the animal may be in motion, or for imaging plants where there may be motion due to the wind or mechanical disturbances. Image reconstruction without motion compensation results in blurred and degraded images, which affects the interpretation and quantitative measurement of radiotracer distribution. Smaller regions of radionuclide accumulation are more difficult to discern. For biological imaging this degradation due to motion influences the measurement of physiological parameters from the radiotracer biodistribution. It would be of great benefit to provide a system for imaging such moving objects, humans and animals, without these blurring artifacts.

OBJECT OF THE INVENTION

It is therefore an object of the present invention to provide a method for imaging moving objects such as humans and animals, without the occurrence of blurring artifacts.

SUMMARY OF THE INVENTION

The present invention provides a method for image reconstruction of moving radionuclide distributions. Its particular embodiment is for single photon emission computed tomography (SPECT) imaging of awake animals, though its techniques are general enough to be applied to other moving radionuclide distributions as well. The invention eliminates motion and blurring artifacts for image reconstructions of moving source distributions. This opens new avenues in the area of small animal brain imaging with radiotracers, which can now be performed without the perturbing influences of anesthesia or physical restraint on the biological system.

DETAILED DESCRIPTION

Figure 1A:
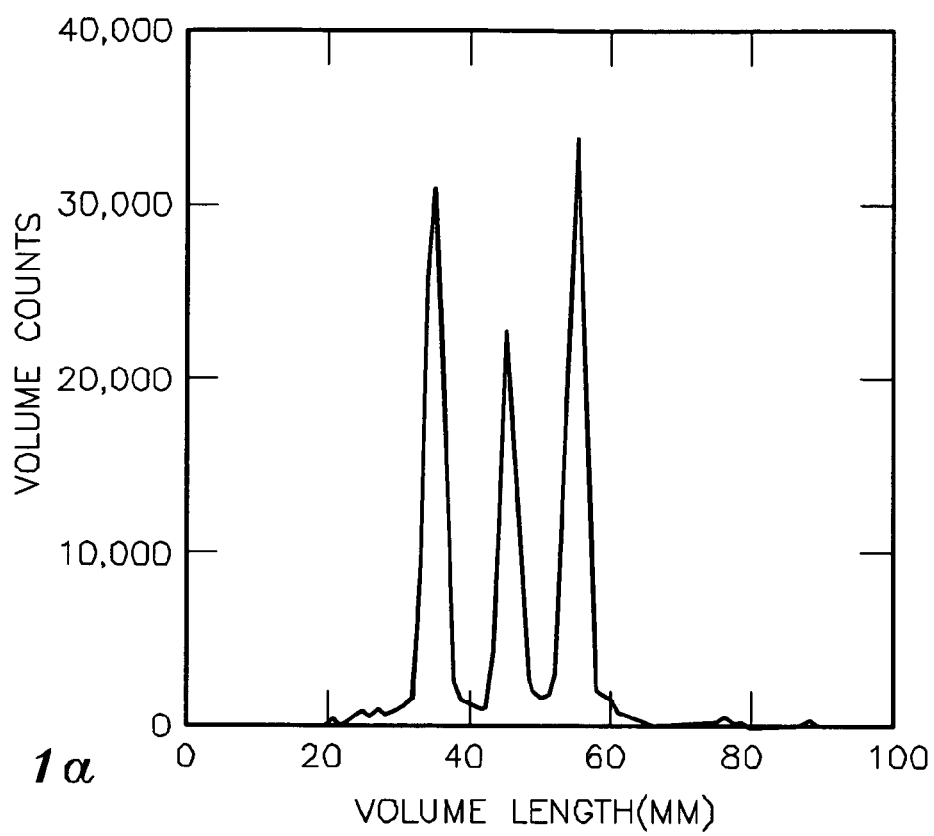
FIGS. 1(a-c) are one-dimensional projections of a reconstructed image volume of: (a) a static phantom data set; (b) a moving phantom data set with motion corrections; and (c) a moving phantom data set without motion corrections.

U.S. Pat. No. 7,209,579 issued Apr. 24, 2007 which is incorporated herein by reference in its entirety, describes a functional imaging system for use in the imaging of unrestrained and non-anesthetized small animals or other subjects and a method for acquiring such images and further registering them with anatomical X-ray images previously or subsequently acquired. The apparatus comprises a combination of an IR laser profilometry system and gamma, PET and/or SPECT, imaging system, all mounted on a rotating gantry, that permits simultaneous acquisition of positional and orientational information and functional images of an unrestrained subject that are registered, i.e. integrated, using image processing software to produce a functional image of the subject without the use of restraints or anesthesia. The functional image thus obtained can be registered with a previously or subsequently obtained X-ray CT image of the subject. That system permitted functional imaging of a subject in an unrestrained/non-anesthetized condition thereby reducing the stress on the subject and eliminating any potential interference with the functional testing that such stress might induce. The method described herein extends and refines the method and the application of the apparatus described in U.S. Pat. No. 7,209,579.

In small animal imaging in accordance with the techniques described in U.S. Pat. No. 7,209,579, image motion is recorded at a rate of 10-15 frames per second, for scan times typically 20-30 minutes. Tomographic SPECT images cannot be obtained for these individual time frames because gamma cameras do not rotate quickly enough to obtain data over 360 degrees. For PET, image reconstructions of individual time frames could be made, rotated and translated in 3-D, and then summed, though the individual frames would be extremely noisy due to the count poor nature of the input data. Summing of a large number of such sub-images to obtain a resultant image has not previously been performed.

The motion correction equation described herein corrects for three-dimensional source motion, rather than just correcting for linear motion of 2-D SPECT projection data, as is sometimes performed for patient motion in SPECT cardiac imaging.

The image reconstruction equation described herein uses all recorded events simultaneously in a unified image reconstruction program that corrects for motion affecting all ray paths.

The image reconstruction method of the present invention in its small animal SPECT brain imaging embodiment uses data from a small animal SPECT scanner whose construction is similar to the device described in U.S. Pat. No. 7,209,579 with certain critical modifications for tomographic SPECT and PET imaging. Firstly, three retroreflectors (not depicted) are glued to the head of the small animal depicted in FIGS. 2, 4-5 and 6-7 of U.S. Pat. No. 7,209,579. A real-time optical tracking system with three cameras provides continuous time stamped pose data of the awake animal head during the SPECT scan, typically 10-15 times/sec. The pose data that is written to a disk file consists of six geometric parameters: three displacements and three angles, with respect to the initial head position. The scintillation events recorded by the gamma camera also are time stamped and written to a file in list-mode. Time-stamped information on the position of the rotating gantry, to which the gamma camera is attached, is written to a third file. The tracking system, gantry and gamma camera clocks are synchronized.

Figure 3:
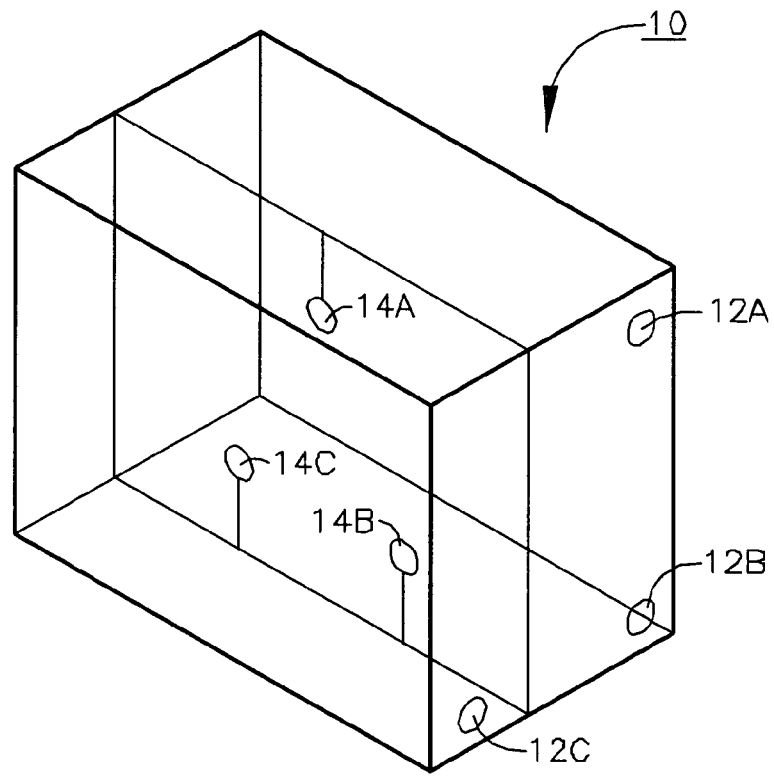
FIG. 3 is a schematic representation of the calibration block used in accordance with the present invention.

A calibration scan is performed prior to imaging of a moving object to determine the transformation between the gamma camera reference frame and the tracking reference frame. The specially designed calibration phantom 10 (see FIG. 3), consisting of three optical markers and three radioactive sources, is scanned in a stationary configuration. This phantom is shown in FIG. 3 and described more fully below. The relative positions of the optical markers and the radioactive sources are known from the phantom design. The data are reconstructed and coordinates of sources in the reconstruction coordinate frame are obtained. A computer program then calculates coordinate transformation between tracking and gamma camera coordinate systems.

Information from the three input files is used in an iterative list-mode maximum likelihood expectation maximization algorithm described below. During image reconstruction the image volume of the activity distribution is transformed from the gamma camera reference frame to the tracking reference frame. A transformation for motion correction is implemented and then the image volume is transformed back to the gamma camera reference frame, in which ray tracing for the iterative reconstruction algorithm is performed.

Figure 4:
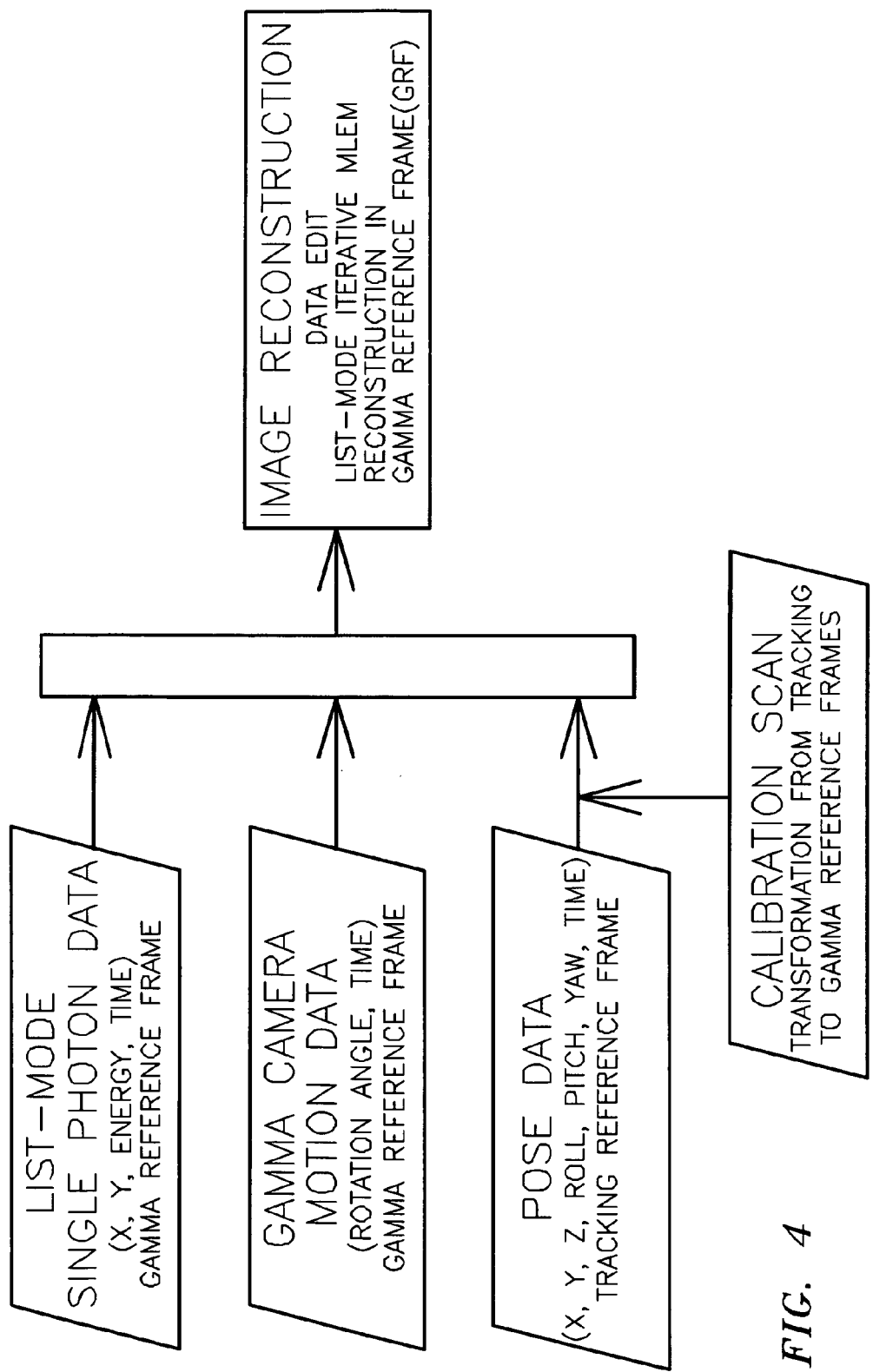
FIG. 4 is a block diagram of the operation of the present invention.

The foregoing process is outlined generally in FIG. 4 wherein it is shown that list-mode single photon data, gamma camera motion data and pose data are integrated with the calibration scan data using the algorithm described below to obtain a reconstructed image of the live unanesthetized animal or subject.

In detail, image is accomplished as follows. Data from all three subsystem files are read in. Projection data are created by histogramming the list-mode data. First, timing intervals during which the gantry is stationary are identified. Next the pose records are compared, and if all six parameters from two successive pose records vary by no more than preset threshold values, the gamma event is added to a 2-D projection image. A new projection image is formed whenever the gamma camera moves or if the pose difference threshold values are exceeded. Note that a threshold value of zero is equivalent to performing no histogramming.

During the iteration steps, the detector is stationary and the reconstruction volume is transformed according to the tracking and gantry location information. A standard iterative maximum likelihood expectation maximization (MLEM) algorithm is utilized, with additional normalization for different acquisition times per projection. The MLEM algorithm used in accordance with the present invention is as follows:

$$s_j^{n+1} = \frac{s_j^n}{\sum_i A_{ij}} \sum_i A_{ij} \left[ \frac{p_{i,meas}}{\sum_k A_{ik} s_k^n} \right].$$

Figure 2:
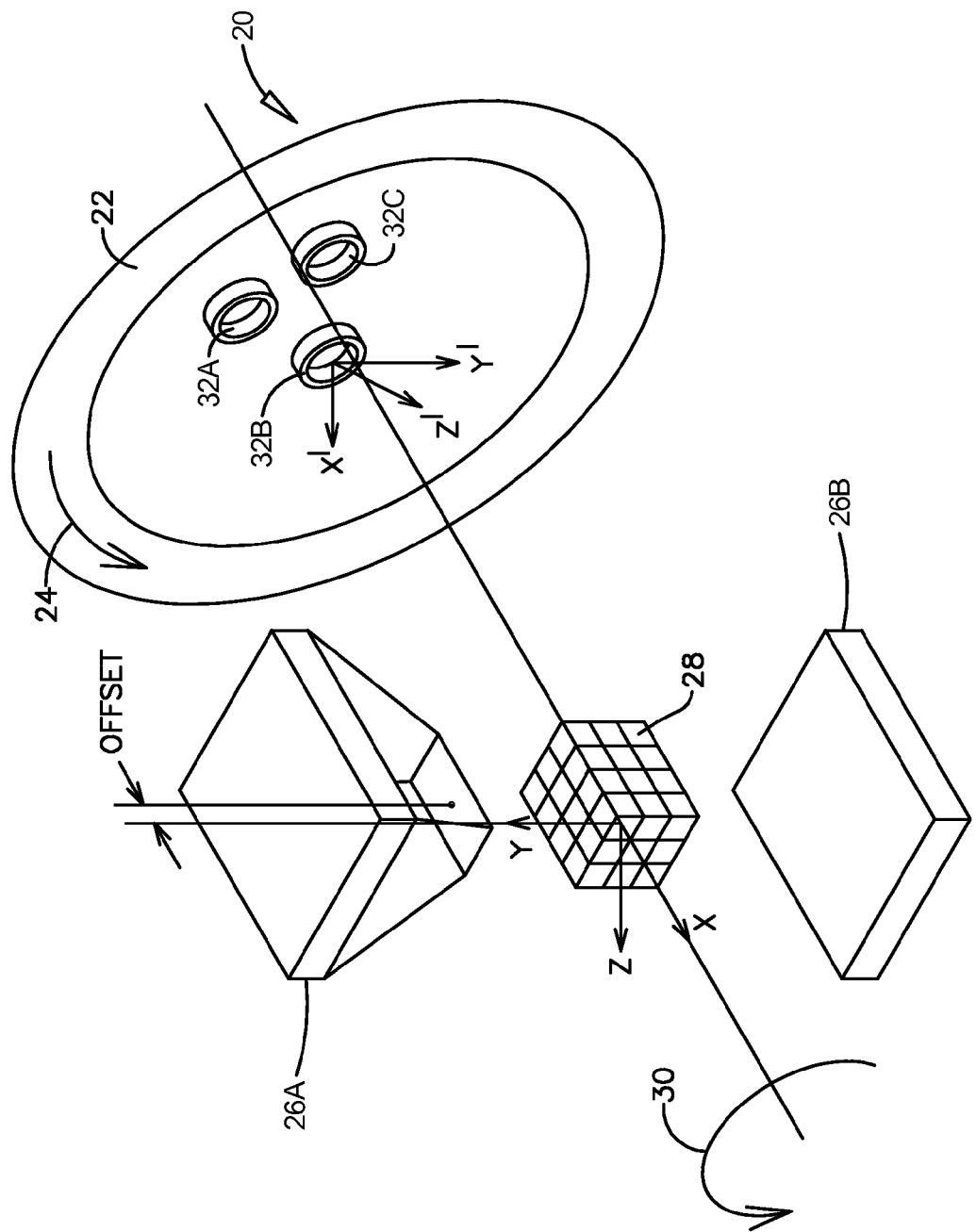
FIG. 2 is a schematic representation of the geometry of the system described herein.

In application, the calibration phantom is imaged with and without motion, and reconstructed with and without motion compensation. The calibration phantom 10 is depicted in FIG. 3 wherein three optical reflectors 12A, 12B and 12C and three $Co^{57}$ point sources 14A, 14B and 14C are provided. FIG. 2 depicts a schematic view of the geometry of the apparatus utilized in accordance with the present invention. A more detailed view of a suitable such apparatus is depicted in the above referenced Figures of U.S. Pat. No. 7,209,579. As shown in FIG. 2, the apparatus 20 comprises a gantry 22 rotating in the direction shown by arrows 24. The positions of gamma cameras 26A and 26B (gamma reference frame GRF) are associated with the SPECT reconstruction volume 28 and the angle of rotation 30. The coordinate system of the GRF is denoted by arrows X, Y, and Z. The positions of gamma cameras 26A and 26B are measured in the GRF. The tracking reference frame (TRF) is defined as the coordinate system of the optical cameras 32A, 32B, and 32C. The coordinate system of the TRF is denoted by arrows $X^I, Y^I$, and $Z^I$.

Image reconstruction is performed in the reference frame of the gamma camera (GRF) and so the position of a point in the source object or animal must be computed as a function of time in this reference frame. From direct measurements with the motion tracking system the object motion is only known as a function of time in the tracking reference frame (TRF), however. The 3-D point position in the GRF can be computed from the motion in the TRF by the vector equation $$x(GRF, t) = R_{TG}[R_{pose}(t)R^{-1}_{pose}(t_0)\{R^{-1}_{TG}[x(GRF, t_0) - t_{TG}] - t_{pose}(t_0)\} + t_{pose}(t)] + t_{TG}$$

wherein:

$x(GRF, t)$ is the 3-D position of a source object point in the gamma reference frame as a function of time t;

$x(GRF, t_0)$ is the 3-D position of a source object point in the gamma reference frame at a starting time $t_0$;

$R_{TG}$ and $t_{TG}$ are the 3-D rotation matrix and the 3-component translation vector describing the transformation from the tracking reference frame to the gamma reference frame; (That is, the coordinates of a point in the gamma reference frame are given by the equation $x(GRF)=R_{TG}x(TRF)+t_{TG}$. The values of $R_{TG}$ and $t_{TG}$ are determined from calibration experiments with a dual modality phantom having retroreflectors and radioactive sources.)

$R^{-1}_{TG}$ is the matrix inverse of $R_{TG}$, so that the coordinates of a point in the tracking reference frame can be computed from the coordinates in the gamma reference frame by the equation $$x(TRF) = R^{-1}_{TG}[x(GRF) - t_{TG}];$$

$R_{pose}(t)$ are $t_{pose}(t)$ are the time-dependent 3-D rotation matrix and the 3-component translation vector describing the motion of a point in the tracking reference frame from a reference position to a position at time t. (The motion tracking system provides this information, which in raw form is given by three rotation parameters (roll, pitch, yaw) and 3 orthogonal translation parameters.)

$R^{-1}_{pose}(t)$ is the inverse of the matrix $R_{pose}(t)$;

$R_{pose}(t_0)$ and $t_{pose}(t_0)$ are the pose rotation matrix and pose translation vector at a time $t_0$ to be used for the object position for image reconstruction. Time $t_0$ is usually taken to be the position at the start of the scan.)

Conceptually the above equation does the following:

1) transforms the coordinates of a source object point in the gamma reference frame at time $t_0$ to its coordinates in the tracking reference frame (using $R^{-1}_{TG}$ and $t_{TG}$);

2) transforms the point position in the tracking reference frame to its position at the reference tracking position (using $R^{-1}_{pose}(t_0)$ and $t_{pose}(t_0)$);

3) applies the measured motion transformation in the tracking reference frame (using $R_{pose}(t)$ and $t_{pose}(t)$); and 4) transforms the coordinates from the tracking reference frame back to the gamma reference frame (using $R_{TG}$ and $t_{TG}$).

Raytracing for forward and backprojection in iterative image reconstruction uses the motion-corrected source voxel positions as given by the above equation, for example in implementations of the maximum likelihood expectation maximization method or the ordered subsets expectation maximization method.

The spatial resolution full width half maximum (FWHM) of the moving point sources with motion correction is only about 0.1 mm worse than that of the point sources imaged without motion. Reconstructions of an awake animal scan with and without motion compensation were performed. Visual comparison of the slices through reconstructed head volumes reveals significant improvement of image quality when motion corrections are implemented. Table 1 below demonstrates Full width at half maximums of profiles taken through each gamma source.

TABLE 1

|  | Static FWHM (mm) | Corrected FWHM (mm) |
|---|---|---|
| Point 1 | 1.93 | 2.07 |
| Point 2 | 2.03 | 2.11 |
| Point 3 | 1.95 | 2.01 |

Figure 1B:
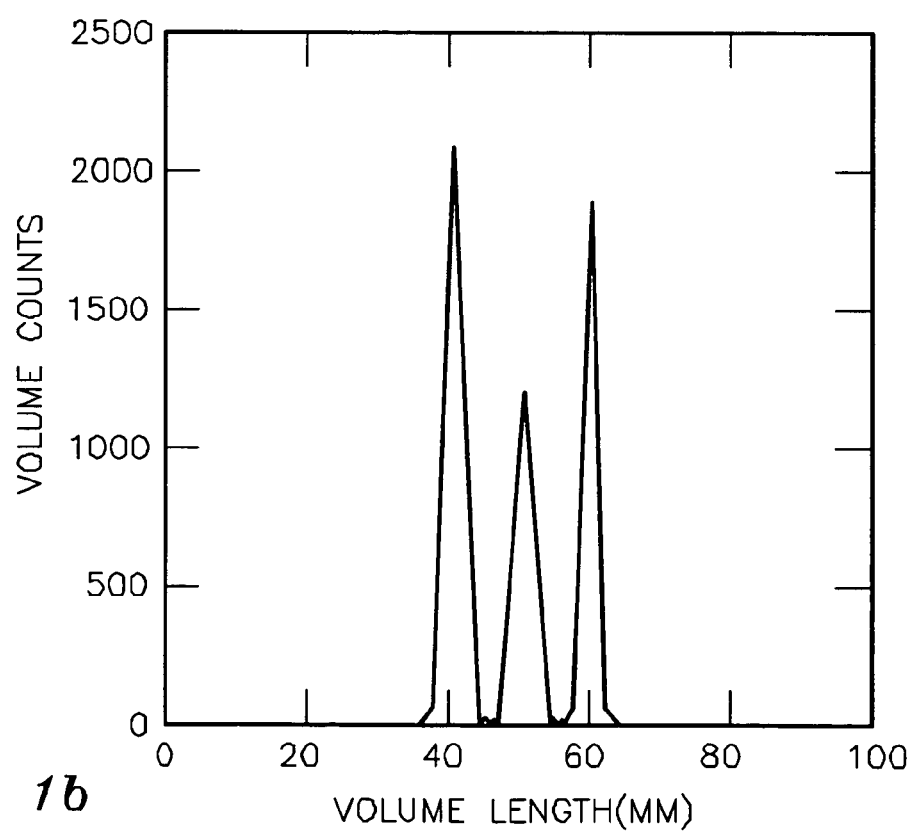
Figure 1C:
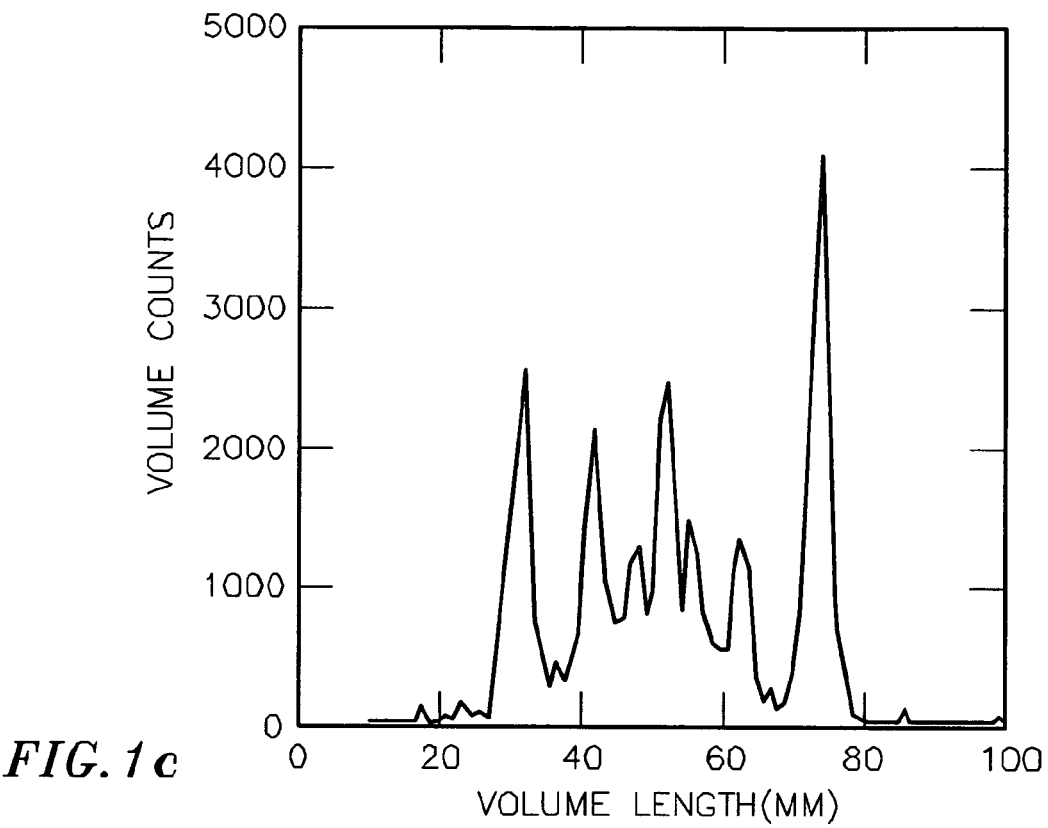

FIGS. 1(a-c) are one-dimensional projections of a reconstructed image volume of: (a) a static phantom data set: (b) a moving phantom data set with motion corrections: and (c) a moving phantom data set without motion corrections.

There has thus been described a method for image reconstruction of moving radionuclide distributions. The invention eliminates motion and blurring artifacts for image reconstructions of moving source distributions. More specifically, the method comprises: A) imaging a three dimensional calibration phantom including at least three reflective markers and at least three gamma sources with and without motion in a tracking system comprising: I) an imaging volume for limited confinement of the subject; II) a rotating gantry about said imaging volume; III) at least three cameras that scan said three dimensional phantom and form an image generated by light reflected from the reflective markers as the cameras scan the subject, to spatially locate the phantom within the imaging volume mounted on the rotating gantry; at least two SPECT and/or PET imaging devices also mounted on the gantry in positions to permit said light sources and said cameras to view said imaging volume and spatially locate and map the phantom while said SPECT and/or PET imaging devices functionally image the phantom; and IV) image processing hardware and software that receive electronic signals from said tracking system and said cameras and generate a combined and registered profile and a functional image of the phantom; and B) repeating the process of step A while a living unanesthetized subject labeled with at least three optical reflectors and having previously been injected with a radiopharmaceutical is located in the imaging volume; and C) obtaining a functional image of the unanesthetized subject through the application of suitable 3-D positioning equations and an iterative list-mode maximum likelihood expectation maximization algorithm that is part of the software.

As will be apparent to the skilled artisan, a number of variations and modifications can be made to the system described above without departing from the spirit and scope of the present invention. All such modifications and changes are clearly contemplated as being within the scope of the invention as defined by the appended claims.

What is claimed is:

1. A method for image reconstruction of moving radionuclide distributions in an unanesthetized living subject comprising:
A) imaging a three dimensional phantom including at least three reflective markers and at least three gamma sources with and without motion in a tracking system comprising:
I) an imaging volume for limited confinement of the phantom;
II) a rotating gantry about said imaging volume;
III) at least three optical cameras that scan said three dimensional phantom, to obtain a tracking reference frame, and form an image generated by light reflected from the reflective markers as the optical cameras scan said phantom, to spatially locate the phantom within the imaging volume mounted on the rotating gantry;
IV) at least two SPECT and/or PET imaging devices mounted on the gantry, to obtain a gamma reference frame, in positions to permit said optical cameras to view said imaging volume and spatially locate and map the phantom while said SPECT and/or PET imaging devices functionally image the phantom; and
V) image processing hardware and software that receive electronic signals from said tracking system and said SPECT and/or PET imaging devices and generate a combined and registered profile and a functional image of the phantom; and
B) repeating the process of step A while the living unanesthetized subject labeled with at least three optical reflectors and having previously been injected with a radiopharmaceutical is located in the imaging volume in place of the phantom; and
C) obtaining a functional image of the unanesthetized living subject through the application of a vector equation and an iterative list-mode maximum likelihood expectation maximization algorithm that is part of the software;
wherein said vector equation is $$x(GRF,t) = R_{TG}[R_{pose}(t)R^{-1}_{pose}(t_0)\{R^{-1}_{TG}[x(GRF,t_0) - t_{TG}] - t_{pose}(t_0)\} + t_{pose}(t)] + t_{TG}$$

and;
x(GRF, t) is a 3-D position of a source object point in the gamma reference frame as a function of time t;
x(GRF, $t_0$) is a 3-D position of a source object point in the gamma reference frame at a starting time $t_0$;
$R_{TG}$ and $t_{TG}$ are a 3-D rotation matrix and a 3-component translation vector describing the transformation from the tracking reference frame to the gamma reference frame;
$R^{-1}_{TG}$ is the matrix inverse of $R_{TG}$;
$R_{pose}(t)$ and $t_{pose}(t)$ are a time-dependent 3-D rotation matrix and a 3-component translation vector describing a motion of a point in the tracking reference frame from a reference position to a position at time t;
$R_{pose}(t_0)$ and $t_{pose}(t_0)$ are a pose rotation matrix and pose translation vector at a time $t_0$ to be used for the object position for image reconstruction; and
$R^{-1}_{pose}(t_0)$ is the inverse of the matrix $R_{pose}(t_0)$.

2. A method for image reconstruction of moving radionuclide distributions in an unanesthetized living subject comprising:
A) attaching at least three retroreflectors to a small animal to be imaged;

B) using a real-time optical tracking system including at least three optical cameras attached to a rotating gantry obtaining continuous time stamped pose data of the unanesthetized living subject to obtain a tracking reference frame;
C) simultaneously performing a SPECT scan using at least two gamma cameras attached to the gantry to obtain time stamped gamma list mode data;
D) simultaneously obtaining time-stamped position information on the position of the rotating gantry;
E) synchronizing the tracking system, gantry and time stamped gamma list mode data;
F) performing a calibration scan to transform from the tracking reference frame to a gamma reference frame; and
G) reconstructing the image in the gamma reference frame through the application of a vector equation and an iterative list-mode maximum likelihood expectation maximization algorithm that is part of the software, wherein said vector equation is $$x(GRF,t) = R_{TG}[R_{pose}(t)R^{-1}_{pose}(t_0)\{R^{-1}_{TG}[x(GRF,t_0) - t_{TG}] - t_{pose}(t_0)\} + t_{pose}(t)] + t_{TG}$$

and;
 x(GRF, t) is a 3-D position of a source object point in the gamma reference frame as a function of time t;
 x(GRF, $t_0$) is a 3-D position of a source object point in the gamma reference frame at a starting time $t_0$;
 $R_{TG}$ and $t_{TG}$ are the 3-D rotation matrix and a 3-component translation vector describing the transformation from the tracking reference frame to the gamma reference frame;
 $R^{-1}_{TG}$ is the matrix inverse of $R_{TG}$;
 $R_{pose}(t)$ and $t_{pose}(t)$ are a time-dependent 3-D rotation matrix and a 3-component translation vector describing a motion of a point in the tracking reference frame from a reference position to a position at time t;
 $R_{pose}(t_0)$ and $t_{pose}(t_0)$ are a pose rotation matrix and pose translation vector at a time $t_0$ to be used for the source object position for image reconstruction; and
 $R^{-1}_{pose}(t_0)$ is the inverse of the matrix $R_{pose}(t_0)$.

* * * * *